US012667393B2

(12) United States Patent
Biedermann et al.

(10) Patent No.: US 12,667,393 B2
(45) Date of Patent: Jun. 30, 2026

(54) RECEIVING PART FOR RECEIVING A ROD FOR COUPLING THE ROD TO A BONE ANCHORING ELEMENT

(71) Applicant: BIEDERMANN TECHNOLOGIES GMBH & CO. KG, Donaueschingen (DE)

(72) Inventors: Lutz Biedermann, Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/314,699

(22) Filed: Aug. 29, 2025

(65) Prior Publication Data

US 2025/0380970 A1      Dec. 18, 2025

Related U.S. Application Data

(63) Continuation of application No. 18/585,577, filed on Feb. 23, 2024, now Pat. No. 12,408,951, which is a (Continued)

(30) Foreign Application Priority Data

Aug. 12, 2009    (EP) ..................................... 09167751

(51) Int. Cl.
    *A61B 17/70*        (2006.01)
(52) U.S. Cl.
    CPC ...... *A61B 17/7037* (2013.01); *A61B 17/7032* (2013.01)
(58) Field of Classification Search
    CPC ............ A61B 17/7032; A61B 17/7034; A61B 17/7037; A61B 17/704
(Continued)

(56) References Cited

U.S. PATENT DOCUMENTS

| | | | |
|---|---|---|---|
| 5,669,911 A | 9/1997 | Errico et al. | |
| 5,672,176 A | 9/1997 | Biedermann et al. | |
| (Continued) | | | |

FOREIGN PATENT DOCUMENTS

| | | | |
|---|---|---|---|
| JP | 2007-502677 A | 2/2007 | |
| WO | WO 2005/018471 A1 | 3/2005 | |
| (Continued) | | | |

OTHER PUBLICATIONS

Office action issued by the USPTO on Dec. 5, 2011 for U.S. Appl. No. 12/709,375, 7 pages.

(Continued)

*Primary Examiner* — Eduardo C Robert
*Assistant Examiner* — Christina Negrellirodriguez
(74) *Attorney, Agent, or Firm* — Womble Bond Dickinson (US) LLP

(57) ABSTRACT

A receiving part for receiving a rod for coupling the rod to a bone anchoring element includes a receiving part body including a first end and a second end, and having a substantially U-shaped recess at the first end forming a channel for receiving the rod, and an accommodation space for accommodating a head of the bone anchoring element, the accommodation space having an opening at the second end for introducing the head; and a pressure element arranged at least partially in the accommodation space, the pressure element including a first section having a second recess for receiving the rod, and a second section having a flexible portion to clamp the head, the first section and the second section being fixed relative to each other, wherein said pressure element is insertable from the opening.

20 Claims, 3 Drawing Sheets

Related U.S. Application Data continuation of application No. 17/493,042, filed on Oct. 4, 2021, now Pat. No. 11,931,079, which is a continuation of application No. 16/538,163, filed on Aug. 12, 2019, now Pat. No. 11,160,582, which is a continuation of application No. 15/872,428, filed on Jan. 16, 2018, now Pat. No. 10,426,522, which is a continuation of application No. 14/878,809, filed on Oct. 8, 2015, now Pat. No. 9,895,172, which is a continuation of application No. 12/855,395, filed on Aug. 12, 2010, now Pat. No. 9,283,000.

(60) Provisional application No. 61/233,406, filed on Aug. 12, 2009.

(58) Field of Classification Search
USPC .................................................. 606/264–272
See application file for complete search history.

(56) References Cited

U.S. PATENT DOCUMENTS

| | | | |
|---|---|---|---|
| 5,797,911 A | | 8/1998 | Sherman et al. |
| 5,879,350 A | | 3/1999 | Sherman et al. |
| 6,053,917 A | | 4/2000 | Sherman et al. |
| 6,063,090 A | * | 5/2000 | Schlapfer ........... A61B 17/7041 |
| | | | 606/270 |
| 6,280,442 B1 | | 8/2001 | Barker et al. |
| 6,368,321 B1 | | 4/2002 | Jackson |
| 6,371,957 B1 | | 4/2002 | Amrein et al. |
| 6,471,705 B1 | | 10/2002 | Biedermann et al. |
| 6,626,906 B1 | | 9/2003 | Young |
| 7,186,255 B2 | | 3/2007 | Baynham et al. |
| 7,211,087 B2 | | 5/2007 | Young |
| 7,291,151 B2 | * | 11/2007 | Alvarez ............. A61B 17/7037 |
| | | | 606/305 |
| 7,322,981 B2 | | 1/2008 | Jackson |
| 7,604,655 B2 | | 10/2009 | Warnick |
| 7,803,174 B2 | | 9/2010 | Denis et al. |
| 7,896,902 B2 | | 3/2011 | Jeon et al. |
| 7,942,910 B2 | | 5/2011 | Doubler et al. |
| 8,016,862 B2 | | 9/2011 | Felix et al. |
| 8,021,398 B2 | | 9/2011 | Sweeney et al. |
| 8,100,909 B2 | | 1/2012 | Butler et al. |
| 8,100,946 B2 | | 1/2012 | Strausbaugh et al. |
| 8,197,517 B1 | | 6/2012 | Lab et al. |
| 8,206,418 B2 | | 6/2012 | Triplett et al. |
| 8,221,472 B2 | | 7/2012 | Peterson et al. |
| 8,361,122 B2 | | 1/2013 | Barrus et al. |
| 8,926,671 B2 | | 1/2015 | Biedermann et al. |
| 11,931,079 B2 | | 3/2024 | Biedermann et al. |
| 2003/0023240 A1 | | 1/2003 | Amrein et al. |
| 2004/0116929 A1 | | 6/2004 | Barker et al. |
| 2005/0070901 A1 | | 3/2005 | David |
| 2005/0203516 A1 | | 9/2005 | Biedermann et al. |
| 2006/0058788 A1 | | 3/2006 | Hammer et al. |
| 2006/0149244 A1 | | 7/2006 | Amrein et al. |
| 2006/0173456 A1 | * | 8/2006 | Hawkes ............. A61B 17/7037 |
| | | | 606/264 |
| 2006/0247624 A1 | | 11/2006 | Banouskou et al. |
| 2006/0271047 A1 | | 11/2006 | Jackson |
| 2007/0118118 A1 | | 5/2007 | Kwak et al. |
| 2007/0288004 A1 | * | 12/2007 | Alvarez ............. A61B 17/7032 |
| | | | 606/86 A |
| 2008/0015580 A1 | | 1/2008 | Chao |
| 2008/0154315 A1 | * | 6/2008 | Jackson ............. A61B 17/7037 |
| | | | 606/301 |
| 2008/0161859 A1 | | 7/2008 | Nilsson |
| 2008/0269809 A1 | | 10/2008 | Garamszegi |
| 2008/0294202 A1 | | 11/2008 | Peterson et al. |
| 2009/0105716 A1 | | 4/2009 | Barrus |
| 2010/0198272 A1 | | 8/2010 | Keyer et al. |
| 2010/0234891 A1 | | 9/2010 | Freeman et al. |
| 2011/0276093 A1 | | 11/2011 | Barrus et al. |
| 2012/0035663 A1 | | 2/2012 | Jackson |
| 2012/0253409 A1 | | 10/2012 | Peterson et al. |
| 2013/0110179 A1 | | 5/2013 | Barrus et al. |

FOREIGN PATENT DOCUMENTS

| | | | |
|---|---|---|---|
| WO | WO 2009/014540 A1 | 1/2009 | |
| WO | WO 2009/015100 A2 | 1/2009 | |

OTHER PUBLICATIONS

Office action issued by the USPTO on Jul. 10, 2012 for U.S. Appl. No. 12/709,375, 6 pages.
Office action issued by the USPTO on Sep. 13, 2013 for U.S. Appl. No. 12/709,375, 6 pages.
Office action issued by the USPTO on Jun. 4, 2014 for U.S. Appl. No. 12/709,375, 5 pages.
European Search Report for European Application No. 09167751.8-1526, European Search Report dated Dec. 15, 2009 and mailed Dec. 23, 2009 (6 pgs.).

* cited by examiner

RECEIVING PART FOR RECEIVING A ROD FOR COUPLING THE ROD TO A BONE ANCHORING ELEMENT

CROSS-REFERENCE TO RELATED APPLICATION(S)

This application is a continuation of U.S. patent application Ser. No. 18/585,577, filed Feb. 23, 2024, which is a continuation of Ser. No. 17/493,042, filed Oct. 4, 2021, now U.S. Pat. No. 11,931,079, which is a continuation of U.S. patent application Ser. No. 16/538,163, filed Aug. 12, 2019, now U.S. Pat. No. 11,160,582, which is a continuation of U.S. patent application Ser. No. 15/872,428, filed Jan. 16, 2018, now U.S. Pat. No. 10,426,522, which is a continuation of U.S. patent application Ser. No. 14/878,809, filed Oct. 8, 2015, now U.S. Pat. No. 9,895,172, which is a continuation of U.S. patent application Ser. No. 12/855,395, filed Aug. 12, 2010, now U.S. Pat. No. 9,283,000, which claims the benefit of U.S. Provisional Patent Application Ser. No. 61/233,406, filed Aug. 12, 2009, the contents of which are hereby incorporated by reference in their entirety, and claims priority to European Patent Application EP 09 167 751.8, filed Aug. 12, 2009, the contents of which are hereby incorporated by reference in their entirety.

BACKGROUND

Field

The invention relates to a receiving part for receiving a rod for coupling the rod to a bone anchoring element. The receiving part includes a receiving part body with a channel for receiving a rod and an accommodation space for accommodating a head of a bone anchoring element, and a pressure element for clamping the head. The accommodation space has an opening at a bottom side for inserting the pressure element and for inserting the head.

Description of Related Art

Various designs of polyaxial bone screws are known wherein a head is clamped from the side to lock a rotational position of the bone screw.

U.S. Pat. No. 5,672,176 describes a bone screw with a receiving part with a conically shaped seat and a conically shaped pressure element which exerts a pressure onto the head from above and from the side.

U.S. Pat. No. 5,669,911 describes a polyaxial orthopaedic device for use with a rod implant apparatus. The device includes a screw having a curvate head, a locking collar disposed therearound, and a receiving member having a linearly tapered socket in which the screw and the collar are nested. The collar is introduced from the top of the receiving member. The head of the screw can be inserted from the bottom.

U.S. Pat. No. 6,063,090 relates to a device used to connect a longitudinal support to a pedicle screw by an accommodating head having a channel to accommodate the longitudinal support. The pedicle screw and the accommodating head are connected via a conical collate chuck in the accommodating head and by a spherical head on the pedicle screw. The device allows engagement of the pedicle screw in the accommodating head after the pedicle screw has been inserted into the bone.

SUMMARY

Embodiments of the invention provide an improved receiving part for receiving a rod for coupling the rod to a bone anchoring element, and a bone anchoring device with such a receiving part, where the embodiments have fewer parts, a low profile, and provide for improved handling during surgery.

Embodiments of the invention provide a receiving part including a receiving part body including a first end and a second end, and having a substantially U-shaped recess at the first end forming a channel for receiving a rod, and an accommodation space for accommodating a head of a bone anchoring element, the accommodation space having an opening at the second end for introducing the head; and a pressure element arranged at least partially in the accommodation space, the pressure element including a first section having a second recess for receiving the rod, and a second section having a flexible portion to clamp the head, the first section and the second section being fixed relative to each other, wherein said pressure element is insertable from the opening, a bone anchoring device including such a receiving part, and a method of using such a receiving part.

For the receiving part according to an embodiment of the invention, the pressure element has a slim design which allows it to be introduced from the bottom into the receiving part body. An internal end stop within the receiving part body may form an abutment for the pressure element to be positioned in an insertion position for the head. Therefore, there may be no additional components for holding the pressure element in the insertion position.

In some embodiments, the receiving part has a low profile and improved or maximum stiffness, since a wall thickness of the receiving part body can be increased due to the slim design of the pressure element.

BRIEF DESCRIPTION OF THE DRAWINGS

Further features and advantages of the invention will become apparent from the description of embodiments using the accompanying drawings. In the drawings.

DETAILED DESCRIPTION

Figures 1, 2:
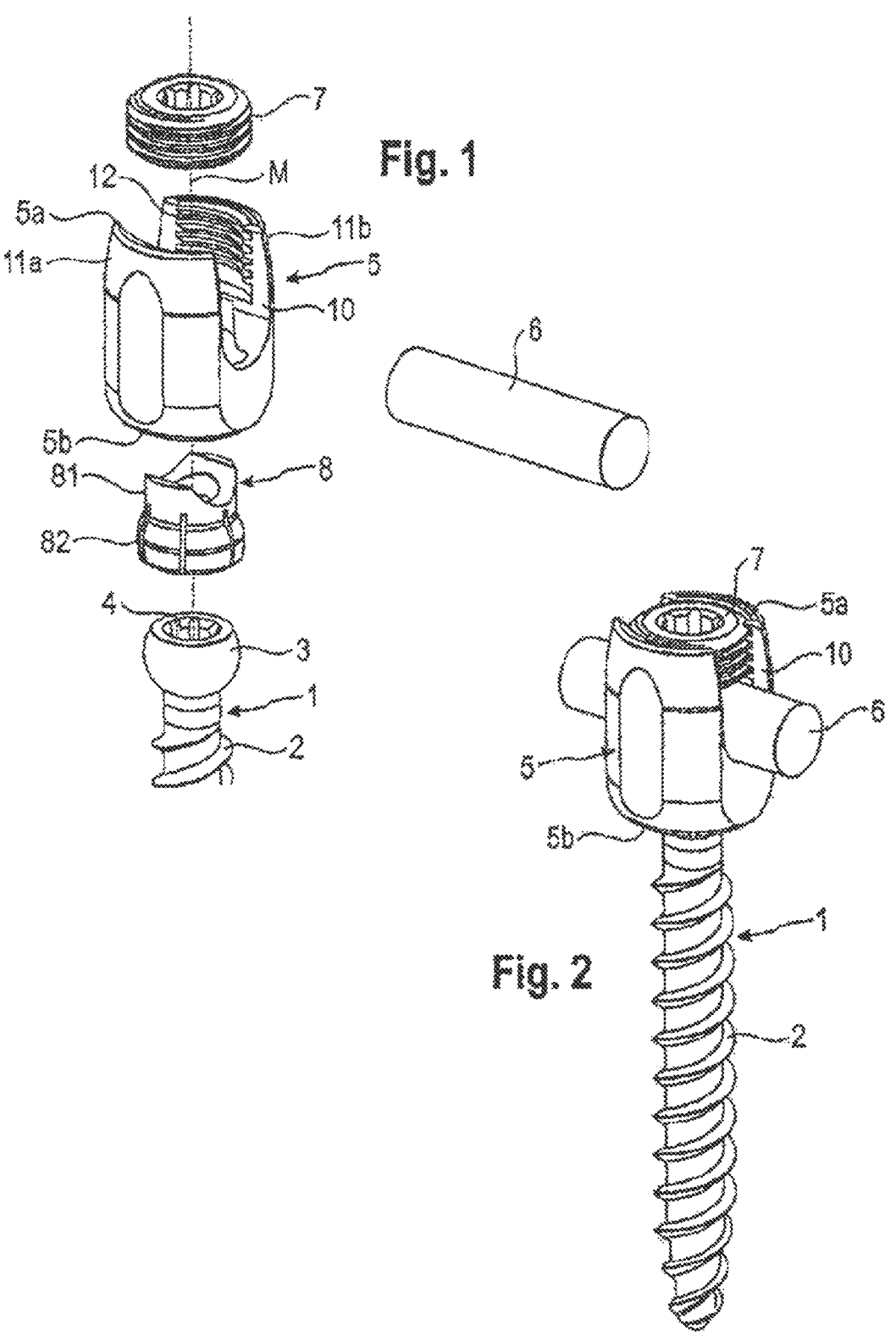
FIG. 1 shows a perspective exploded view of a first embodiment of the bone anchoring device.
FIG. 2 shows a perspective view of the bone anchoring device of FIG. 1 in an assembled state.

As shown in FIGS. 1 and 2, a bone anchoring device according to a first embodiment includes a bone anchoring element 1 in the form of a bone screw having a threaded shaft 2 and a head 3, which in this embodiment is a spherical segment-shaped head. The head 3 has a recess 4 for engagement with a screwing-in tool. The bone anchoring device further includes a receiving part body 5 for receiving a rod 6 to connect the rod to the bone anchoring element 1. Further, a closure element 7, in the form of an inner screw or set screw in some embodiments, is provided for securing the rod 6 in the receiving part body 5. In addition, the bone anchoring device includes a pressure element 8 for locking the head 3 in the receiving part body 5.

The receiving part body 5 is now explained with reference to FIGS. 1 to 3. The receiving part body 5 includes a first end 5*a* and a second end 5*b*, and an axis of symmetry M passes through the first and the second end. A bore 9, which is coaxial with the axis of symmetry M, extends from the first end 5*a* to the second end 5*b*. The bore 9 may have a smallest diameter at, about, or adjacent to its middle section 91 in a center region of the receiving part body 5. In a first region adjacent to the first end 5*a*, the receiving part body 5 has a U-shaped recess 10, which may be symmetric with respect to the symmetry axis M. The recess 10 has a bottom which may be directed towards the second end 5*b* and provides two free lateral legs 11*a*, 11*b* extending towards the first end 5*a*. In the region of the legs 11*a*, 11*b* an internal thread 12 may be provided which may cooperate with the closure element 7, which in this embodiment is a set screw. A channel formed by the U-shaped recess 10 is sized so as to receive the rod 6 therein, the rod for connecting a plurality of bone anchoring devices.

At a second region near the second end 5*b*, the receiving part body 5 has a narrowing portion 13, which narrows in a direction towards the second end 5*b*. The narrowing portion 13 provides a seat for the screw head and the pressure element. The narrowing portion 13 is located at a distance from the second end 5*b* to, for example, enable the screw shaft 2 to be pivoted in a certain pivot angle range. An opening 14 is provided at the second end 5*b*, the diameter of which may be the same as or larger than the diameter of the narrowing portion 13 in some embodiments. Between the narrowing portion 13 and the middle portion 91 of the bore 9, a portion with an inner diameter larger than the diameter of the narrowing portion 13 is provided, which forms a space 15 for allowing the pressure element to expand, as described later. At its side opposite to the narrowing portion 13, the space 15 connects to the middle section 91 of the bore 9 having the smaller diameter, thereby providing a circular shoulder 16.

The middle section 91 of the bore 9 includes a circular projection 17 at its side opposite to the space 15, which can also act as a stop, as described below in more detail.

Figure 3:
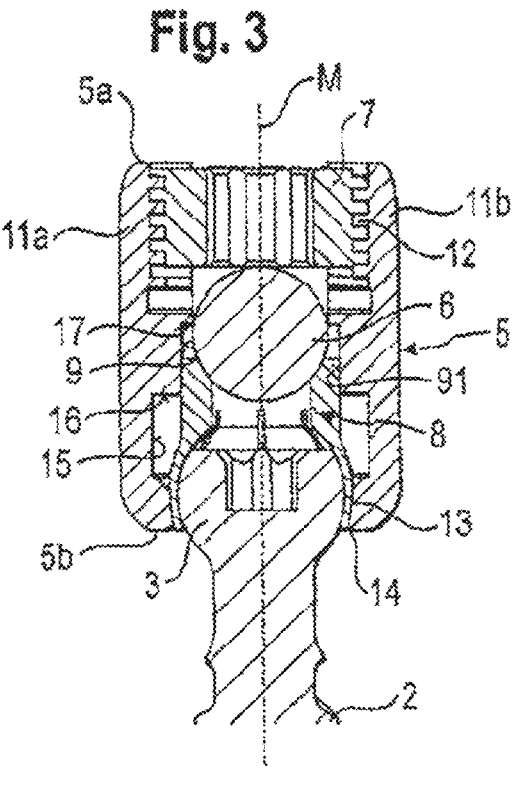
FIG. 3 shows a cross-sectional view of the bone anchoring device of FIG. 1, the section being taken perpendicular to a rod axis.
Figure 4:
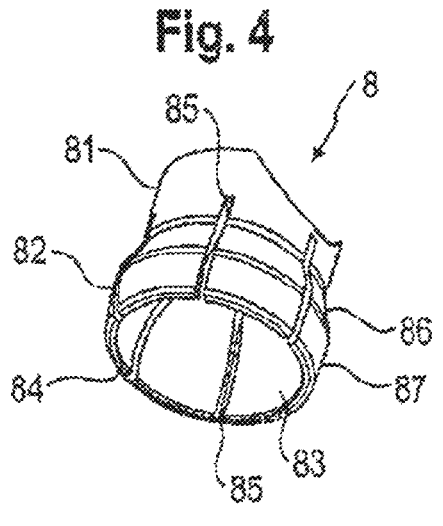
FIG. 4 shows an enlarged perspective view of a pressure element according to an embodiment of the bone anchoring device.
Figure 5:
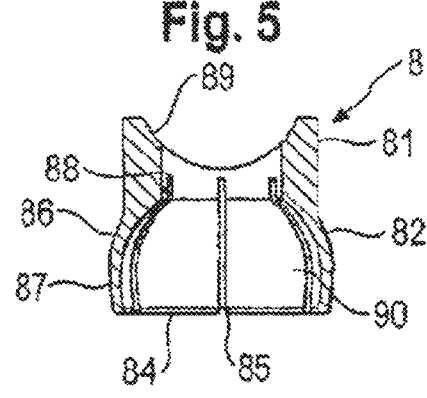
FIG. 5 shows a cross-sectional view of the pressure element according to FIG. 4.
Figure 6:
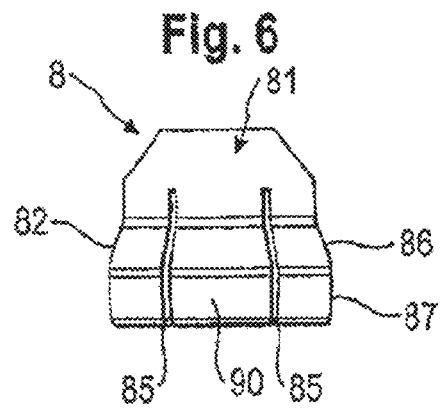
FIG. 6 shows a side view of the pressure element of FIG. 4.
Figure 7:
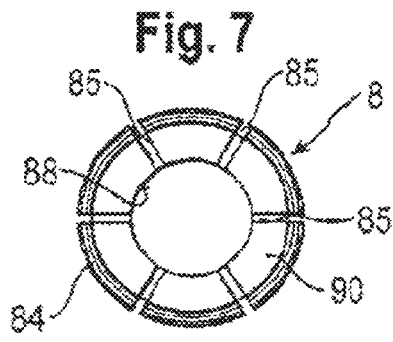
FIG. 7 shows a bottom view of the pressure element of FIG. 4.

As can be seen in FIGS. 1 and 3 to 7, a pressure element 8 according to an embodiment of the invention includes a first section 81 which is substantially cylindrical and has an outer diameter which may be slightly smaller than the inner diameter of the middle section 91 of the bore 9, so that the pressure element 8 is movable in the bore 9. It further has a second section 82, which has a hollow interior 83 which is substantially spherically-shaped and is sized to clamp the spherical head 3 therein. The outer diameter of the first section 81 may be, as can be seen in FIG. 3, smaller than an outer diameter of the head 3 and a largest outer diameter of the second section 82 is greater than the outer diameter of the cylindrical section 81. A free end of the second section 82 provides an opening 84 for introduction of the head 3. Further, the second section 82 may have a plurality of slits 85 extending from the edge of the opening 84 through the second section 82 to define or form slightly resilient legs 90. The number and the dimension of the slits 85 may be such that the wall of the second portion is flexible enough to snap onto the head 3 when the head 3 is being inserted. The slits 85 can extend into the first cylindrical section 81 as shown in the figures to enhance flexibility. The outer wall surface of the second section 82 may include a first portion 86 which may be spherically-shaped, and a second portion 87 adjacent to the opening 84 which may be tapered or curved or otherwise narrowing towards the opening 84. The portion 87 cooperates with the narrowing portion 13 of the receiving part body when the head is locked in the receiving part body.

Further, the pressure element has a coaxial bore 88 for providing access to the screw head by a tool. The first section 81 may have at its free end a cylindrically-shaped or cylinder segment-shaped recess 89 for receiving the rod 6 therein.

The dimensions of the pressure element 8 are such that the pressure element 8 can be inserted through the opening 14 at the second end 5*b* of the receiving part body 5, with the cylindrical first section 81 inserted first. When the second section 82 passes through the opening 14, it may be compressed due to the flexibility of the second section 82, or the legs 90 thereof, which allows the pressure element 8 to be fully introduced into the receiving part body 5.

The pressure element 8 can be pushed into the receiving part body 5 until an upper edge of the first section 81 abuts against the stop 17 provided by the annular projection in the receiving part body 5. When the pressure element is in this position, the flexible second section 82 is located in the portion between the middle section 91 of bore 9 and the narrowing portion 13 of the receiving part body 5. In this position, a free space in the space 15 between the outer wall of the second section 82 of the pressure element and the inner wall of the receiving part body 5 provides room for the flexible second section 82 to expand when the head 3 is inserted.

A depth of the cylindrical recess 89 of the pressure element is smaller than a radius of the rod 6, so that the pressure element can be pressed down by means of screwing-in the inner screw 7, which presses onto the rod 6, which in turn presses onto the pressure element 8. The pressure element 8 is oriented in the receiving part body 5 such that its cylindrical recess 89 is aligned with the U-shaped recess of the receiving part body 5.

The material of which the components of the bone anchoring device are made is preferably a body compatible metal, such as stainless steel or titanium, or a body compatible alloy such as a nickel titanium alloy, in particular Nitinol. However, body compatible plastic materials, such as medical-grade polyether ether ketone (PEEK), can also be used.

In use, first, the pressure element 8 is introduced via the bottom opening 14 into the receiving part body 5 until it abuts against stop 17. This can be done either by the surgeon, or before so that the receiving part body is preassembled with the pressure element 8. Thereafter, the head 3 is introduced through the bottom opening and pushes the pressure element 8 upwards against stop 17. This is the insertion position, which allows the screw head 3 to be introduced through the opening 84 into the pressure element 8, thereby widening the hollow interior 83, or the legs 90 respectively, until the pressure element 8 snaps onto the head 3. This can be done either before screwing the threaded shaft 2 into the bone, or after having screwed in the threaded shaft 2 into the bone, to mount the receiving part body 5, with the pressure element inside, onto the head 3. When the head 3 is inserted, it can still pivot within the pressure element 8 if the flexible section 82 is not compressed. A plurality of bone anchoring devices may be implanted into the bone(s), for example, in the pedicles of adjacent vertebrae, and the rod 6 may be inserted into the bone anchoring devices, respectively. Angular positions of the receiving part bodies may then be adjusted. Finally, the set screw 7 for each bone anchoring device may be tightened, thereby pressing down the rod 6 onto the respective pressure elements, which are pressed down until the second portion 87 of the outer wall of the second section 82 of each pressure element engages with the narrowing portion 13 of the respective receiving part bodies. In this condition, the head of each bone anchoring device is clamped in an interior of the pressure element, so that it is locked in a desired angular position.

Figure 8A:
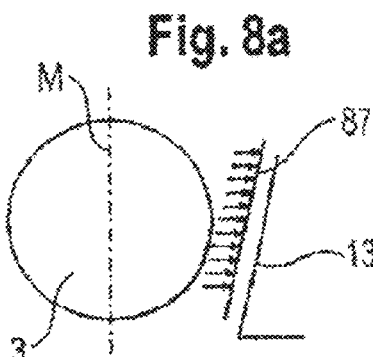
FIGS. 8a to 8d show schematic views of design modifications of a pressure element and a receiving part body in a locking position according to embodiments of the bone anchoring device.
Figure 8B:
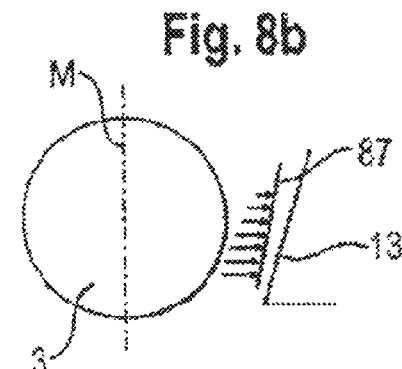
Figure 8C:
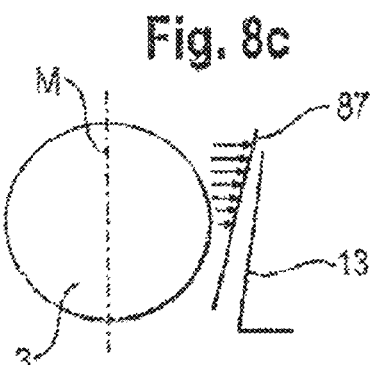
Figure 8D:
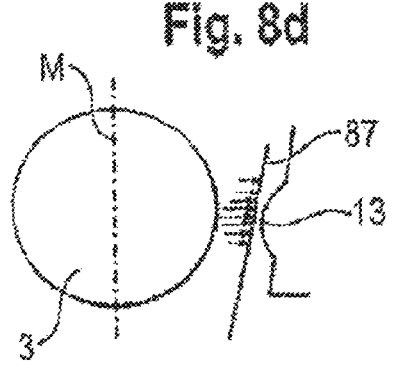

FIGS. 8a to 8d show various designs of the narrowing portion 13 of the receiving part body 5 and the portion 87 of the pressure element 8 which engages the narrowing portion 13 according to embodiments of the invention. FIG. 8a shows the two portions tapering lineally at substantially a same angle. This provides a substantially even pressure distribution between the second portion 87 of the pressure element 8 and the narrowing portion 13 of the receiving part body 5. FIG. 8b and FIG. 8c show two different designs where the respective portions are tapered at different angles. FIG. 8b shows a main contact area at a bottom of the narrowing portion 13, and FIG. 8c shows a main contact area at a top of the narrowing portion 13. FIG. 8d shows a tapering second portion 87 of the pressure element 8 and a rounded portion 13 of the receiving part body, wherein a curvature of the rounded portion is directed towards a center of the receiving part body 5. With such a configuration, a contact area positioned at the rounded portion can be achieved.

Figure 9A:
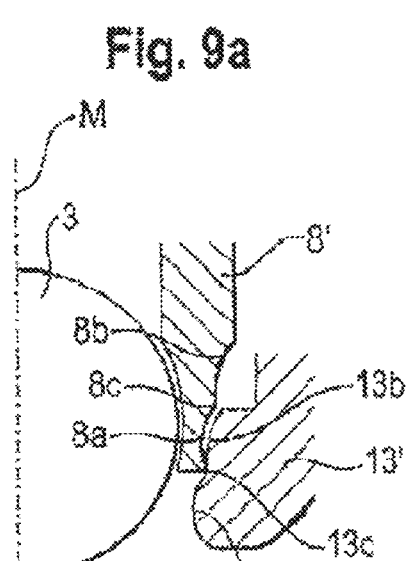
FIGS. 9a and 9b show schematic views of a further design modification of the pressure element and the receiving portion in a pre-locking position and a locking position, respectively, according to an embodiment of the bone anchoring device.
Figure 9B:
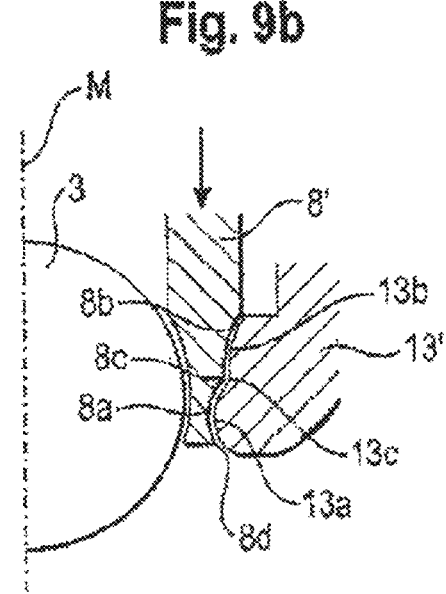

In FIGS. 9a and 9b a narrowing portion 13' of a modified example of a receiving part body 5 has a double spherical radius formed by two curved portions 13a, 13b on top of (i.e., adjacent to) each other, with a groove 13c therebetween. A curvature of the curved portions are directed towards the central axis M. Correspondingly, a modified pressure element 8' has at its lower end two invertedly curved portions 8a, 8b which correspond to the curved portions 13a, 13b, with a crest 8c therebetween, and an outer crest 8d at an outer yielding edge of the pressure element 8'.

As shown in FIG. 9a, when the pressure element 8' moves downward, its lower most edge 8d engages in the groove 13c. In this position there is a frictional clamping of the head 3, which still allows the head 3 to be pivoted upon exertion of a force, where this force is greater than a force needed to pivot the head 3 when the head 3 is introduced in an insertion position. This may be characterized as a pre-locking condition. As shown in FIG. 9b, by further pressing the pressure element 8' downward, the curvatures of the pressure element 8' engage with the corresponding curvatures of the narrowing portion 13' to finally lock the head 3.

Further modifications of the bone anchoring device are possible. For example, in one embodiment the pressure element 8 can have a recess corresponding to the cylindrical recess 89 described above, which may be U-shaped and provides legs extending above the rod. A dual part closure element can then be used to separately clamp the head and the rod. A device for preventing the pressure element from rotating can be provided (not shown). Such a device can be realised, for example, by crimp bores or by a pin extending from the wall into a recess (not shown) of the pressure element.

Further, in some embodiments, the abutment or stop 17, on which a pressure element may abut after it is inserted through the bottom opening and pushed further inwards, can be provided at other locations in the receiving part, for example, at the circular shoulder 16, which may then interact with a corresponding projecting part of the pressure element to provide an abutment for the pressure element.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
a bone anchoring element comprising a shaft and a head;
a receiving part for receiving a rod for coupling the rod to the bone anchoring element, the receiving part comprising:
a receiving part body having a first end, a second end, a channel at the first end for receiving the rod, an engagement surface for engagement with a separate closure element for locking the rod in the channel, an accommodation space for accommodating the head of the bone anchoring element, and an opening at the second end sized for inserting the head therethrough into the accommodation space; and
a seat insertable through the opening of the receiving part body and positionable at least partially in the accommodation space to engage and hold the head in the accommodation space;
wherein when the seat is in the receiving part body at an insertion position, the head of the bone anchoring element is insertable through the opening of the receiving part body into the accommodation space;
wherein the seat is adjustable from the insertion position to a pre-locking position to restrict the head from being removed from the receiving part body through the opening, where the seat is pivotable together with the receiving part body relative to the head, and where the seat abuts against another part of the bone anchoring device to restrict movement of the seat back towards the insertion position; and
wherein the bone anchoring device is further adjustable to lock the head relative to the receiving part body.

2. The bone anchoring device of claim 1, wherein the seat is expandable.

3. The bone anchoring device of claim 2, wherein when the seat is at the pre-locking position, the seat is restricted from expanding to restrict the head from being removed from the receiving part body through the opening.

4. The bone anchoring device of claim 1, wherein the receiving part further comprises a rod engaging portion with a rod contacting surface configured to extend into the channel of the receiving part body to contact the rod.

5. The bone anchoring device of claim 4, wherein the seat and the rod engaging portion are movable together in the receiving part body.

6. The bone anchoring device of claim 4, wherein the seat and the rod receiving portion are formed as respective parts of a monolithic pressure element.

7. The bone anchoring device of claim 1, wherein when the seat is at the pre-locking position and the head is held in the seat, a frictional force is configured to be exerted on the head to temporarily hold an angular position of the head relative to the receiving part body.

8. A bone anchoring device comprising:
a bone anchoring element comprising a shaft and a head;

B2

7 a receiving part for receiving a rod for coupling the rod to the bone anchoring element, the receiving part comprising:

a receiving part body having a first end, a second end, a channel at the first end for receiving the rod, an engagement surface for engagement with a separate closure element for locking the rod in the channel, an accommodation space for accommodating the head of the bone anchoring element, and an opening at the second end sized for inserting the head therethrough into the accommodation space; and a seat insertable through the opening of the receiving part body and positionable at least partially in the accommodation space to engage and hold the head in the accommodation space;

wherein when the seat is in the receiving part body, the head of the bone anchoring element is insertable past the opening of the receiving part body to the seat;

wherein the seat is adjustable to a pre-locking position to restrict the head from being removed from the receiving part body through the opening, where the seat is pivotable together with the receiving part body relative to the head, and where the seat is configured to be held at the pre-locking position while the channel for the rod is vacant or unobstructed; and wherein the bone anchoring device is further adjustable to lock the head relative to the receiving part body.

9. The bone anchoring device of claim 8, wherein the seat is expandable.

10. The bone anchoring device of claim 9, wherein when the seat is at the pre-locking position, the seat is restricted from expanding to restrict the head from being removed from the receiving part body through the opening.

11. The bone anchoring device of claim 8, wherein the receiving part further comprises a rod engaging portion with a rod contacting surface configured to extend into the channel of the receiving part body to contact the rod.

12. The bone anchoring device of claim 11, wherein the seat and the rod receiving portion are formed as respective parts of a monolithic pressure element.

13. A bone anchoring device comprising:

a bone anchoring element comprising a shaft and a head;

a receiving part for receiving a rod for coupling the rod to the bone anchoring element, the receiving part comprising:

a receiving part body having a first end, a second end below the first end, a channel at the first end for receiving the rod, an accommodation space for accommodating the head of the bone anchoring element, and an opening at the second end sized for inserting the head therethrough into the accommodation space; and a seat insertable through the opening of the receiving part body and positionable at least partially in the accommodation space to engage and hold the head in the accommodation space;

wherein when the head of the bone anchoring element and the seat are in the receiving part body, the seat is movable downwardly to a pre-locking position to restrict the head from being removed from the receiving part body through the opening, where the seat is pivotable together with the receiving part body relative to the head, and where an engagement between the seat and another surface of the receiving part that is positioned axially lower than a bottom of the channel of the receiving part body restricts upward movement of the seat away from the pre-locking position; and wherein the bone anchoring device is further adjustable to lock the head relative to the receiving part body.

14. The bone anchoring device of claim 13, wherein the seat is expandable.

15. The bone anchoring device of claim 14, wherein when the seat is at the pre-locking position, the seat is restricted from expanding to restrict the head from being removed from the receiving part body through the opening.

16. The bone anchoring device of claim 13, wherein the receiving part further comprises a rod engaging portion with a rod contacting surface configured to extend into the channel of the receiving part body to contact the rod.

17. The bone anchoring device of claim 16, wherein the seat and the rod receiving portion are formed as respective parts of a monolithic pressure element.

18. The bone anchoring device of claim 16, wherein the rod contacting surface of the rod engaging portion forms a U-shaped recess with an axial depth that is less than half of a greatest width of the U-shaped recess.

19. The bone anchoring device of claim 13, wherein the seat is further configured to assume an insertion position where the head of the bone anchoring element is insertable through the opening into the receiving part body, and wherein the seat is movable downwardly from the insertion position to the pre-locking position.

20. The bone anchoring device of claim 13, wherein the seat engages a surface of the receiving part body at the pre-locking position to restrict the upward movement of the seat.

* * * * *